United States Patent
Handschuck et al.

(10) Patent No.: US 8,066,960 B2
(45) Date of Patent: Nov. 29, 2011

(54) METHOD AND DEVICE FOR AN ACCELERATED OXIDATION TEST OF FUELS OR PETROLEUM PRODUCTS, AS WELL AS A COMPUTER PROGRAM FOR CONTROLLING SUCH A DEVICE, AND A CORRESPONDING COMPUTER READABLE STORAGE MEDIUM

(75) Inventors: Bernhard Handschuck, Berlin (DE); Christian Heine, Berlin (DE); Andrea Neumann, Hoenow (DE); Ruediger Schulz, Berlin (DE); Volkmar Wierzbicki, Berlin (DE)

(73) Assignee: Petrotest Instruments GmbH Co. KG, Dahlewitz (DE)

( * ) Notice: Subject to any disclaimer, the term of this patent is extended or adjusted under 35 U.S.C. 154(b) by 538 days.

(21) Appl. No.: 11/454,139

(22) Filed: Jun. 16, 2006

(65) Prior Publication Data

US 2006/0286674 A1    Dec. 21, 2006

(30) Foreign Application Priority Data

Jun. 17, 2005   (DE) .......................... 10 2005 028 896

(51) Int. Cl.
*B01L 3/02*    (2006.01)
(52) U.S. Cl. ....................................... 422/522; 73/61.67
(58) Field of Classification Search .................. None
See application file for complete search history.

(56) References Cited

U.S. PATENT DOCUMENTS

| | | | |
|---|---|---|---|
| 5,427,334 A | * | 6/1995 | Rauscher, Jr. .............. 244/172.2 |
| 6,127,185 A | | 10/2000 | Melton et al. |
| 6,244,738 B1 | * | 6/2001 | Yasuda et al. ................. 366/114 |

FOREIGN PATENT DOCUMENTS

| | | |
|---|---|---|
| DE | 197 46 723 | 4/1999 |
| JP | 02-43293 | 2/1990 |

(Continued)

OTHER PUBLICATIONS

Sharma, B.K. et al. Soybean oil based greases: Influence of composition on thermo-oxidative and tribochemical behavior, 2005, Journal of Agricultural and Food Chemistry, vol. 53, pp. 2961-2968.*

Cerny, Jaroslav, and Zelinka, Miroslav: "Oxidation Stability of Lubricants Measured by a PDSC Technique", Petroleum and Coal, 2004, 46 (3), pp. 56-62.

(Continued)

*Primary Examiner* — Yelena G Gakh
*Assistant Examiner* — Robert Xu
(74) *Attorney, Agent, or Firm* — Pearl Cohen Zedek Latzer, LLP (57) ABSTRACT

A device and a method for an accelerated oxidation test of fuels or petroleum products, as well as a computer program for controlling such a device, and a corresponding computer readable storage medium, which are applicable, in particular, for the simulation of the aging of fuels or petroleum products. A device for an accelerated oxidation test of fuels or petroleum products is proposed, whereby the device comprises of a pressure vessel (1) to hold specimen (2) of fuels or petroleum products, and the pressure vessel (1) contains at least one device to change the temperature. A corresponding method provides that a specimen (2) of fuel or petroleum product is placed in a pressure vessel (1), the specimen is brought to a predefined temperature above 100° C. by at least one device to change the temperature, which is placed in the pressure vessel (1) and/or in the specimen (2), and the absolute pressure value is monitored so as to determine the oxidation.

5 Claims, 5 Drawing Sheets

FOREIGN PATENT DOCUMENTS

| | | |
|---|---|---|
| JP | 05-66557 | 3/1993 |
| JP | 07-191017 | 7/1995 |
| JP | 07-248291 | 9/1995 |
| JP | 2005-507025 | 3/2005 |
| WO | WO 03/035806 | 5/2003 |

OTHER PUBLICATIONS

Sharma, Brajendra K. et al: "Development of a new oxidation stability test method for lubricating oils using high-pressure differential scanning calorimetry", Thermochimica Acta 402, 2003, pp. 1-18.

"Testing of Liquid Fuels: Determination of Oxidation Stability", DIN 51 780, Jul. 1963.

\* cited by examiner

Fig. 4 ously described breaking point. Furthermore, the pressure vessel does not need to be placed in a water bath, but the heat is introduced directly into the specimen which also reduces the time duration as well.

METHOD AND DEVICE FOR AN ACCELERATED OXIDATION TEST OF FUELS OR PETROLEUM PRODUCTS, AS WELL AS A COMPUTER PROGRAM FOR CONTROLLING SUCH A DEVICE, AND A CORRESPONDING COMPUTER READABLE STORAGE MEDIUM

RELATED APPLICATION DATA

The present application claims priority from prior German application 10 2005 028 896.0, filed on Jun. 27, 2005, incorporated herein by reference in its entirety.

FIELD OF THE INVENTION

The invention relates to a method and a device for an accelerated oxidation test of fuels or petroleum products, as well as a computer program for controlling such a device, and a corresponding computer readable storage medium, which are applicable, in particular, for the simulation of the aging of fuels or petroleum products.

BACKGROUND

The international standards, such as, for example, DIN 51 780 (outdated), (EN) ISO 7536 or ASTM D 525, exist for the determination of the oxidation period, for example, of fuels. These standards stipulate that a 50 ml fuel specimen is placed and sealed in a pressure vessel with specified deviations, and is charged with oxygen to a pressure of 700 kPa so as to determine the time of the pressure drop setting-in later on, which presents the standardized oxidation result.

Conventionally, a device for an accelerated oxidation test of fuels and petroleum products is provided with a pressure gauge, and is placed in a water bath tempered at 100° C. Under these conditions (increased temperature, as well as oxygen under pressure effect), the fuel usually oxidizes considerably faster than under normal storage, which allows conclusions to be drawn regarding the lifespan of the fuel expected under normal ambient conditions in this regard.

The manual or automatic evaluation takes place on the basis of the oxidation that sets in after some time, which, according to the standards, is defined as the breaking point with 14 kPa pressure drop in 15 minutes, and in automatic detection, leads to the recording of curves/data.

In case of present day fuels, the breaking points, under the above mentioned test conditions, typically lie around 6 . . . 8 hours, which has to be felt as very disadvantageous, if one compares these periods with those of the other laboratory tests for the dispatch release, which are mostly made within minutes. Furthermore, there are fuels, whose additives decelerate the oxidation in such a manner that the slope described in the standard ASTM D 525 for the result sought is not achieved.

Thermal processes are applied as additional techniques, such as, for example, the dynamic Heat Flux or the dynamic Differential Scanning Calorimetry (DSC), and/or the Pressure Differential Calorimetry (PDSC) in which the heat flux of a small sample quantity is determined under defined measuring conditions. Thereby, a local temperature increase in the specimen compared with the environment indicates an oxidation.

Consequently, the problem of the invention was to provide a method and a device for an accelerated oxidation test of fuels or petroleum products, as well as a computer program to control such a device, and a corresponding computer readable storage medium, which eliminate the above mentioned deficiencies and, in particular, allow to reduce the time duration for the determination of the breaking point.

SUMMARY OF THE INVENTION

The invention relates to a device and a method for an accelerated oxidation test of fuels or petroleum products, as well as a computer program for controlling such a device, and a corresponding computer readable storage medium, which are applicable, in particular, for the simulation of the aging of fuels or petroleum products For this purpose, a device for an accelerated oxidation test of fuels or petroleum products is proposed, whereby the device comprises of a pressure vessel (1) to hold specimen (2) of fuels or petroleum products, and the pressure vessel (1) contains at least one device to change the temperature. A corresponding method provides that a specimen (2) of fuel or petroleum product is placed in a pressure vessel (1), the specimen is brought to a predefined temperature above 100° C. by at least one device to change the temperature, which is placed in the pressure vessel (1) and/or in the specimen (2), and the absolute pressure value is monitored so as to determine the oxidation.

According to the invention, this problem is solved through the features in the specification set forth below.

One embodiment includes a method for an accelerated oxidation test of fuels or petroleum products, whereby a specimen of a fuel- or petroleum product is placed in a pressure vessel, characterized in that the specimen (2) is brought to a predefined temperature above 100° C. by at least one device to change the temperature, which is placed in the pressure vessel (1) and/or in the specimen (2), and the pressure in the pressure vessel is monitored so as to determine the oxidation.

One embodiment includes a method characterized in that the predefined temperature is held constant during the oxidation test.

One embodiment includes a method characterized in that a specimen (2) to a volume of 3 to 20 ml is placed.

One embodiment includes a method characterized in that the pressure vessel (1) and/or the specimen (2) are impacted with ultrasonic.

One embodiment includes a device for an accelerated oxidation test of fuels or petroleum products, whereby the device comprises of a pressure vessel to hold specimen of fuels or petroleum products, characterized in that the pressure vessel (1) comprises of at least one device to change the temperature, whereby the pressure vessel (1) and at least that one device to change the temperature are arranged in such a manner that the specimen (2) is impacted directly with heat.

One embodiment includes a device characterized in that at least that one device to change the temperature is developed as a heater (6).

One embodiment includes a device characterized in that at least that one device to change the temperature is placed in the pressure vessel (1) and/or in the specimen (2).

One embodiment includes a device characterized in that the internal wall of the pressure vessel (1) at least partially shows a resistant surface.

One embodiment includes a device characterized in that the resistant surface is constructed of gold.

One embodiment includes a device characterized in that an ultrasonic vibrator is placed at the bottom of the pressure vessel (1) and/or in the specimen (2).

One embodiment includes a computer program, which upon being loaded in the memory of the data processing unit, enables a data processing unit to execute a process for an accelerated oxidation test of fuels or petroleum products, whereby a specimen of a fuel or petroleum product is placed in a pressure vessel, and the specimen (2) is brought to a predefined temperature above 100° C. by at least one device to change the temperature, which is placed in the pressure vessel (1) and/or in the specimen (2), and the pressure in the pressure vessel (1) is monitored so as to determine the oxidation.

One embodiment includes a computer readable storage medium on which a program is stored, which, upon being loaded in the memory of the data processing unit, makes it feasible for a data processing unit to execute a method for an accelerated oxidation test of fuels or petroleum products, whereby a specimen of a fuel or petroleum product is placed in a pressure vessel, and the specimen (2) is brought to a predefined temperature above 100° C. by at least one device to change the temperature, which is placed in the pressure vessel (1) and/or in the specimen (2), and the pressure in the pressure vessel (1) is monitored so as to determine the oxidation.

One embodiment includes a computer readable storage medium on which a computer program or parts of a computer program to carry out methods discussed herein are stored.

One embodiment includes a process with which a computer program is downloaded from an electronic data network, for example, from Internet, to a data processing unit connected to the data network.

BRIEF DESCRIPTION OF THE DRAWINGS

The invention is described in detail below with reference to the figures of the drawings on embodiments. It shows:

FIG. 1 a, b Reproduction and illustration of an embodiment of the pressure vessel according to the invention, FIG. 2 Diagram for the explanation of recording of the breaking point, FIG. 3 Diagrammatic representation of the design, and mode of functioning of the device according to the invention, FIG. 4 Illustration of the passive surface of the pressure vessel.

DETAILED DESCRIPTION OF THE INVENTION

According to the invention, a method for an accelerated oxidation test of fuels or petroleum products is characterized in that a specimen of the fuel or petroleum product is placed in a pressure vessel, and the specimen is brought to a desired temperature through at least one device to change the temperature, which is placed in the pressure vessel and/or in the specimen, and upon achievement of the given temperature, the pressure in the pressure vessel is monitored so as to determine the oxidation. According to the invention, a temperature above 100° C. is given thereby. Preferably, the predefined temperature is kept constant during the oxidation test. The oxidation of the fuel and/or the petroleum product is determined by identifying the breaking point by monitoring the absolute pressure value.

It is provided in a preferred embodiment of the method according to the invention that a specimen to a volume of 3 to 20 ml is placed. Preferably, a specimen to a volume of approximately 5 ml is placed.

It is further provided in a preferred embodiment of the method according to the invention that the pressure vessel and/or the specimen are impacted with ultrasonic.

A special advantage of the device according to the invention for an accelerated oxidation test of fuels or petroleum products is that a very rapid change of temperature, in particular, a quick increase of temperature, is effected. This is achieved by having the device, which comprises a pressure vessel to hold the specimen of fuels or petroleum products, and the pressure vessel contains at least one device to change the temperature, whereby the pressure vessel and at least that one device to change the temperature are arranged in such a manner that the specimen is directly charged with heat. In a preferred embodiment, small thermal quantities are applied, whereby the process is accelerated further on.

It is intended in a preferred embodiment of the device according to the invention that at least one device is designed as heater to change the temperature. Preferentially, a heater with a control device is installed. Thereby, at least that one device to change the temperature can be placed in the pressure vessel and/or in the specimen.

It is intended in another preferred embodiment of the device according to the invention that the internal wall of the pressure vessel at least partially show a resistant surface. For example, the pressure vessel can be constructed from aluminum, and the resistant surface can be constructed of gold.

It is intended in a further preferred embodiment of the device according to the invention that an ultrasonic vibrator is placed at the bottom of the pressure vessel and/or in the specimen.

To control the device according to the invention, preferentially a computer program is deployed. Such a computer program according to the invention for an accelerated oxidation test, upon being loaded in the memory of the data processing unit, enables a data processing unit to execute a process for an accelerated oxidation test of fuels or petroleum products, whereby a specimen of a fuel or petroleum product is placed in a pressure vessel, and the specimen is brought to a predefined temperature above 100° C. by means of at least one device to change the temperature, which is placed in the pressure vessel and/or in the specimen, and the pressure in the pressure vessel is monitored so as to determine the oxidation.

In the marketing of the invention it can be of advantage, if such a computer program (against fee or free of charge, freely accessible or password-protected) is made available for downloading in a data- or communications network. The computer program made available in such a manner could then be taken advantage of through a process with which a computer program according to Claim 11 is downloaded from an electronic data network, such as, for example, from Internet to a data processing unit connected to the data network.

In order to carry out the method for an accelerated oxidation test of fuels and petroleum products according to the invention, it is intended to install a computer readable storage medium on which a program is stored, which, upon being loaded in the memory of the data processing unit, makes it feasible for a data processing unit to execute a method for an accelerated oxidation test of fuels or petroleum products, whereby a specimen of a fuel or petroleum product is placed in a pressure vessel, and the specimen is brought to a predefined temperature above 100° C. by at least one device to change the temperature, which is placed in the pressure vessel and/or in the specimen, and the pressure in the pressure vessel is monitored so as to determine the oxidation.

Additionally or alternatively, computer readable storage mediums could be made available on which a computer program according to Claim 11 or parts of a computer program according to Claim 11 are stored.

The invention shows the following advantages:

Accelerated Method:

The invention proposes to accelerate the standardized test by increasing the temperature. Thereby, it was identified that an increase in temperature from 100° C. to 140° C. can lower the oxidation period to approximately 7% of the value.

An important precondition for this is a faster heat transfer to the specimen. It is intended in the Standard-Method that the fuel should firstly be placed in a glass envelope, and then this unit should be placed in the pressure vessel, whereby a quick heat flow in the material, which is to be tested, is obstructed.

Passive Surface in the Pressure Vessel:

That is why a basic approach of this accelerated method is to place the fuel directly in the pressure vessel—without glass envelope—. The chemical/physical/catalytic effects are prevented through a resistant surface, for example, of gold (compare FIG. 4), during the direct contact of the fuel with the metal now.

Tempering Block:

After closing the pressure vessel, it is not placed in a liquid bath anymore, rather the pressure vessel's metal block (hereinafter briefly referred to as "Block") with the specimen is quickly and accurately brought to the desired temperature by a built-in temperature controlled heater (compare FIG. 1b)

The sensor for this control is in the block or in the fuel specimen itself. In this manner, a good reproducible temperature behavior is achieved.

Recording of Changed Breaking Point:

Fuels, which are present in the market today, as a rule, have an increasingly greater lifespan with regard to their oxidation resistance. Through this, it can happen that because of the too low decreasing slopes of the oxidation pressure possibly connected therewith, no breaking point according to the conventional definition is produced, although the fuel reacts with the oxygen.

Figure 2:
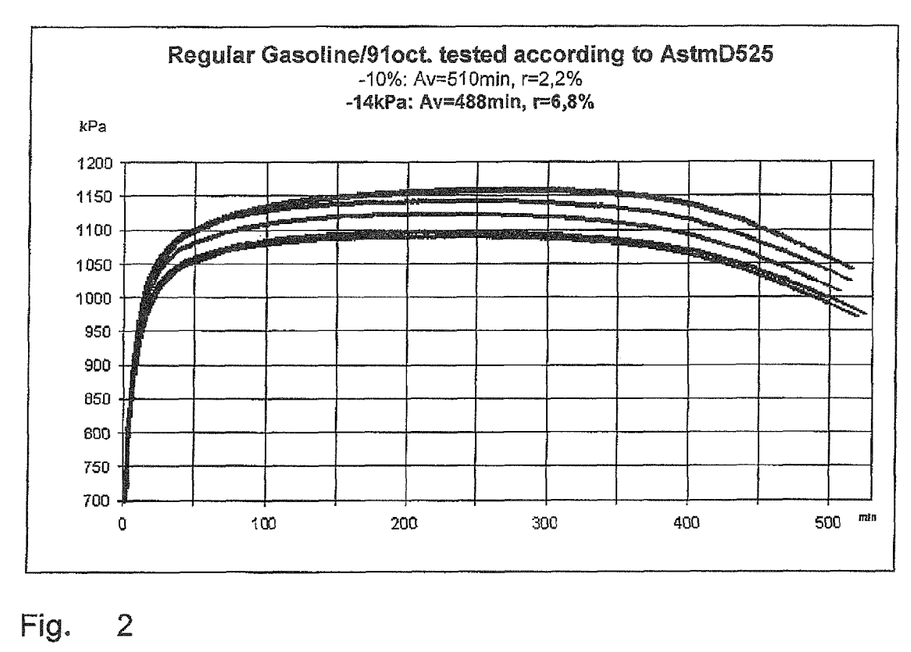

Furthermore, it can be easily identified from the curves presented in FIG. 2 that even in case of the established test, this breaking point is only vaguely determinable because of the relatively flat drop in pressure.

The breaking point is, therefore, determined in the accelerated method by monitoring the absolute pressure value. It is achieved when the pressure has dropped by 10% from its achieved maximum value—independent of the Sink Rate—.

It appears from FIG. 2 that the repeatability "r" in the accelerated method with 2.2% vis-à-vis 6.8% is significantly better. The breaking point results of both the methods somewhat deviate from each other in the mean value (Av).

Improvements of the Accelerated Method vis-à-vis the Standard Method:

|  | Standard Method | Accelerated Method |
| --- | --- | --- |
| Cleaning of the pressure vessel | yes | yes |
| Filling-in of the specimen 50/5 ml | 50 ml | 5 ml |
| Close the cover of the pressure vessel | yes | yes |
| Flush 1 time with oxygen | app. 3 min | automatic |
| Finally bring-in oxygen | 1 min | automatic |
| Initial pressure of the oxygen that is brought in | 700 kPa | 500 kPa |
| Hot start in liquid bath/heating block | app. 1 min (Bath) | auto. (Block) |
| Constant oxidation temperature | 100° C. | 140° C. |
| Monitoring of gas leakage | automatic | automatic |
| Recording the end of oxidation (auto.) | app. <500 min | app. <45 min |
| Recording the presence for cooling-off | app. 1 min | automatic |

-continued

|  | Standard Method | Accelerated Method |
| --- | --- | --- |
| Slow drainage of oxidized gas | 2 min | automatic |
| Total volume of the pressure vessel | app. 160 ml | app. 20 ml |
| Specimen quantity | 50 ml | 5 ml |
| Ultrasonic Mixer possible? | no | yes |

Improved Safety:

In a preferred embodiment, the volume of the block and of the specimen (Accelerated Method) was selected about 10 times lesser than the Standard Method. This led to it that even the energies released as a result of an unintentional, but not completely ruled out explosion of the highly inflammable oxygen-fuel mixture, accordingly decrease.

The same increase in the temperature would considerably increase this risk in the standard method. Tests have shown that this energy is discharged relatively slow through a rupture disc specified for it, and because of the jets of fire coming out with it, can endanger the operating personnel. However, because the described accelerated methods run automatically, the presence here during the entire heating period can be dispensed with. The handling takes place only after the cooling-off process. In the Standard Method, this presence for In- and Output is requisite.

Ultrasonic Agitating:

For further acceleration of the oxidation behavior and/or for the better intermixing of the specimen, an impacting by ultrasonic can be provided. For instance, for this purpose, an ultrasonic vibrator can be provided at the bottom or directly in the specimen.

The invention is supposed to be exemplified in great details in the following. The invention is exemplified by the embodiment example of the determination of oxidation of fuel. However, the invention is not restricted to it, rather in place of fuel, even other petroleum products could also be tested with the method according to the invention.

Figure 1A:
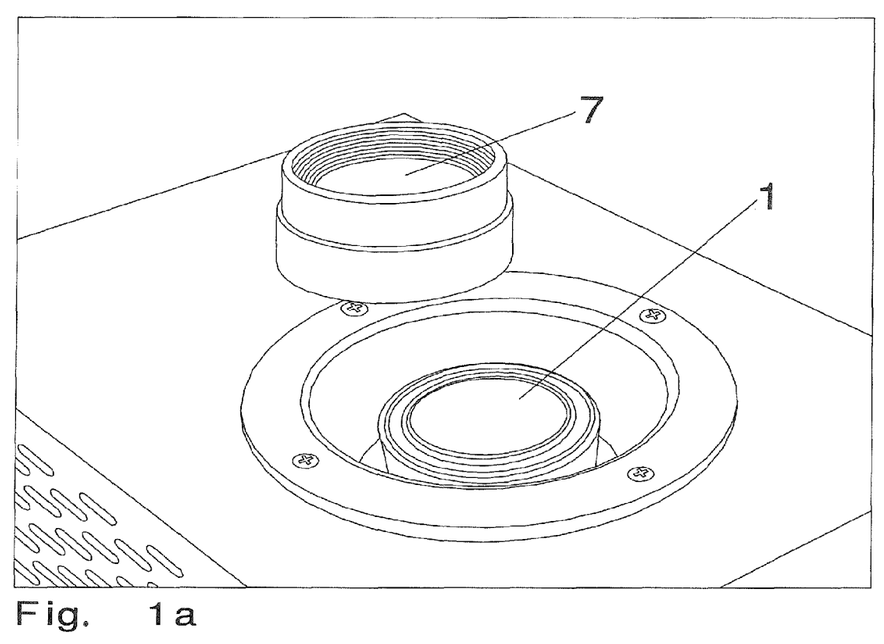
Figure 1B:
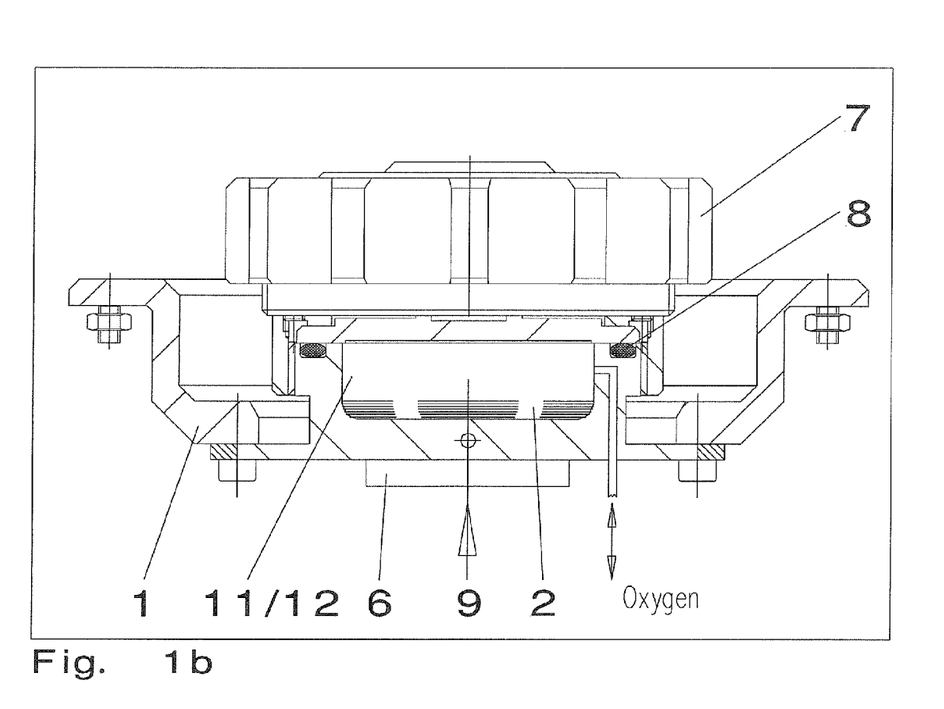

Design of the Device (Compare FIG. 1 a, b):

As is obvious from FIG. 1b, an exemplary pressure vessel 1 according to the invention having a screw cap 7 with seal 8, which tightly closes the pressure vessel 1. The (temperature controlled) heater 6 is placed at the bottom of the pressure vessel 1. Alternatively, the heater 6 can also be placed in the exemplary fuel specimen 2. The temperature is monitored by a temperature sensor 9.

Figure 4:
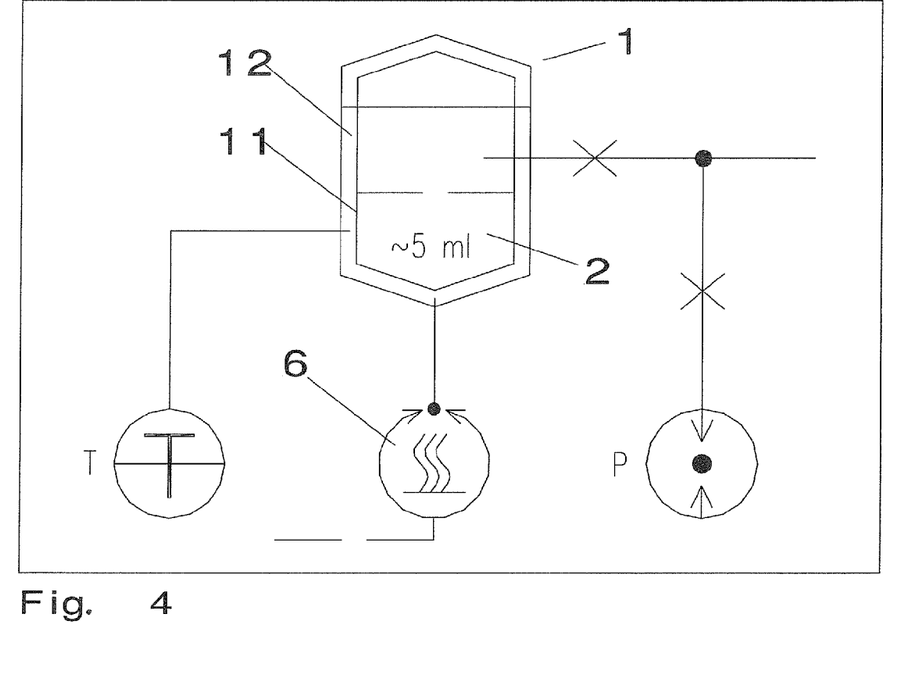

For prevention of chemical/physical/catalytic effects between the fuel specimen 2 and the pressure vessel 1, which could emerge, if the fuel specimen 2 is given directly in the pressure vessel 1 without the glass envelope, the internal wall of the pressure vessel 1 is provided with a resistant surface 11 in a preferred embodiment. The wall 12 of the pressure vessel 1 can be composed of a nonresistant material, for example, aluminum.

Figure 3:
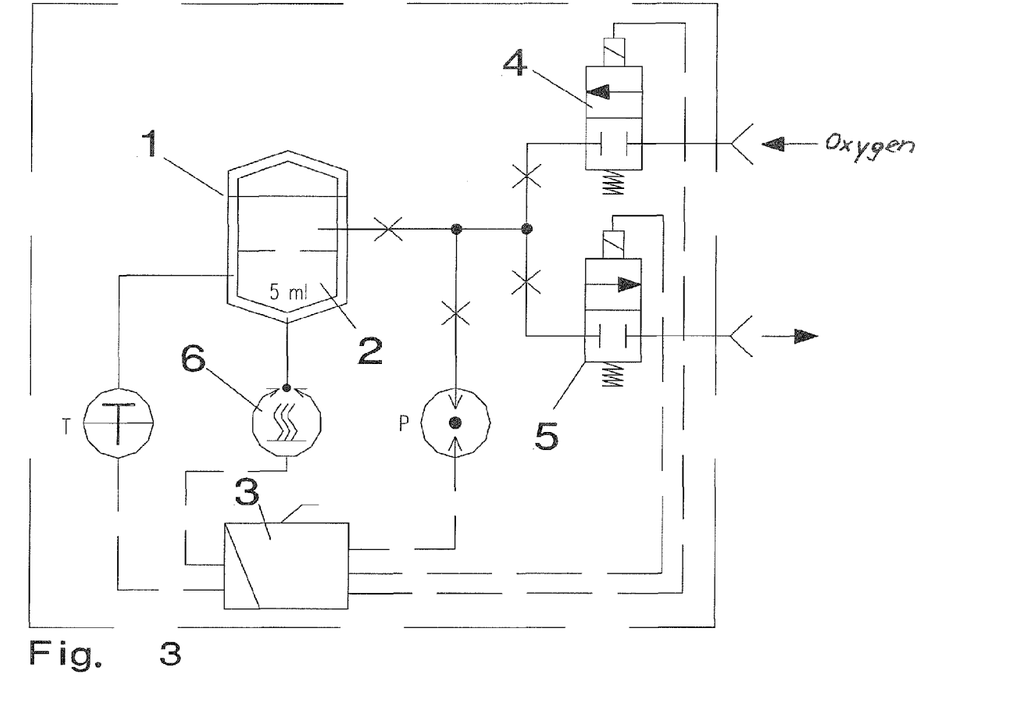

Description of the Program-Flow (Compare FIG. 3):

After its cleaning, the pressure vessel 1 (Reaction Vessel) is filled up with 5 ml fuel specimen 2 (Pipette, if need be, through automatic feed).

The cap the pressure vessel 1 is screwed up in a gas-tight manner. The program is delayed-start through a control unit 3 (Control- and Operating Unit) so that the user has the opportunity to distance himself from the device.

The control unit 3 opens the inlet valve 4 (Filling Valve) till the pressure sensor P registers the filling pressure of 500 kPa.

The control unit 3 opens the outlet valve 5 (Purging) till the pressure sensor P registers the ambient pressure.

The control unit 3 opens the inlet valve 4 (Filling Valve) till the pressure sensor p registers the filling pressure of 500 kPa.

The heater 6 (Heater) is operated by the control unit 3 as long as the temperature sensor T signals the preset-temperature (140° C.).

Simultaneously, the measurement/registering of time and pressure is started.

Upon achieving the preset-temperature, for example, 140° C., the maximum developed pressure is registered as Pmax.

When the pressure falls below Pmax−10% (breaking point found), a blower fan is switched on for re-cooling.

If the desired temperature falls close to the room temperature, firstly, the remaining pressure is discharged, and subsequently, the user is signaled so that the pressure vessel 1 can be opened for cleaning.

| List of Reference Numbers | |
|---|---|
| 1 | Pressure Vessel |
| 2 | Specimen, Fuel Specimen |
| 3 | Control Unit |
| 4 | Inlet Valve |
| 5 | Outlet Valve |
| 6 | Heater |
| 7 | Screw Cap |
| 8 | Seal [Sealing Gasket] |
| 9 | Temperature Sensor |
| 11 | Resistant Surface |
| 12 | Wall of the Pressure Vessel |

The invention in its embodiment does not restrict to the above-mentioned preferred embodiment example. On the contrary, a number of variants are conceivable, which can make use of the device according to the invention, and the method according to the invention, even with the types of fundamentally different nature.

The invention claimed is:

1. A device for an accelerated oxidation test of fuels or petroleum products, the device comprising:
    a data processing device,
    a pressure vessel to hold specimen of the fuels or the petroleum products, the pressure vessel comprising at least one temperature changing device,
    wherein the at least one temperature changing device constitutes a part of the bottom of the pressure vessel or the at least one temperature changing device is placed at the bottom of the pressure vessel,
    where the internal surface of the pressure vessel at least partially is provided with a surface resistant against at least one of chemical, physical and catalytic effects between the specimen and the pressure vessel, and
    where the data processing device is configured for executing a method for an accelerated oxidation test of fuels or petroleum products, the method comprising:
        bringing the specimen, which is placed in the pressure vessel, to a predefined temperature above 100° C. using the at least one temperature changing device, and
        monitoring the pressure in the pressure vessel and determining the breaking point by a predefined percentage of the drop of pressure with respect to the maximum of the absolute pressure value.

2. The device according to claim 1, wherein the at least one temperature changing device comprises a heater.

3. The device according to claim 1, wherein the resistant surface comprises gold.

4. The device according to claim 1 comprising an ultrasonic vibrator.

5. The device according to claim 4 wherein the ultrasonic vibrator is disposed in the specimen.

* * * * *

UNITED STATES PATENT AND TRADEMARK OFFICE
CERTIFICATE OF CORRECTION

| | | |
|---|---|---|
| PATENT NO. | : 8,066,960 B2 | Page 1 of 1 |
| APPLICATION NO. | : 11/454139 | |
| DATED | : November 29, 2011 | |
| INVENTOR(S) | : Bernhard Handschuck et al. | |

It is certified that error appears in the above-identified patent and that said Letters Patent is hereby corrected as shown below:

On the title page item (73), should read:

--Assignee: Petrotest Instruments GmbH & Co. KG--

Signed and Sealed this
Twenty-eighth Day of February, 2012

David J. Kappos
*Director of the United States Patent and Trademark Office*